United States Patent [19]

Edelberg et al.

[11] 4,038,995
[45] Aug. 2, 1977

[54] HAIR TREATING COMPOSITION CONTAINING A MINK OIL FATTY ACID QUATERNARY AMMONIUM SALT

[75] Inventors: Norman L. Edelberg, Des Plaines; Chester A. Davis, Berwyn, both of Ill.

[73] Assignee: Helene Curtis Industries, Inc., Chicago, Ill.

[21] Appl. No.: 661,950

[22] Filed: Feb. 27, 1976

[51] Int. Cl.² .......................... A45D 7/04; A61K 7/09
[52] U.S. Cl. ........................................ 132/7; 8/127.51; 424/70; 424/71
[58] Field of Search ............... 424/71, 70; 8/127.51; 132/7; 260/561 N

[56] References Cited

U.S. PATENT DOCUMENTS

| | | | |
|---|---|---|---|
| 3,899,288 | 8/1975 | Galerne | 424/71 X |
| 3,912,808 | 10/1975 | Sokol | 424/71 |

*Primary Examiner*—Albert T. Meyers
*Assistant Examiner*—Vera C. Clarke
*Attorney, Agent, or Firm*—Dressler, Goldsmith, Clement, Gordon & Shore, Ltd.

[57] ABSTRACT

An improved hair treating composition for waving and straightening hair is provided. The novel composition comprises from about 0.5 to about 15 percent by weight of a reducing agent selected from the group consisting of ammonium and sodium sulfites and bisulfites and from about 0.1 to about 5.0 percent by weight of a quaternary ammonium salt of a mink oil fatty acid and has a pH between 6.5 and 6.9.

10 Claims, No Drawings

HAIR TREATING COMPOSITION CONTAINING A MINK OIL FATTY ACID QUATERNARY AMMONIUM SALT

BACKGROUND OF THE INVENTION

This invention relates to hair treating compositions for permanent waving or straightening the hair and more specifically relates to improved compositions containing a quaternary ammonium salt of mink oil fatty acids as the conditioning agent.

It is known that the configuration of hair can be altered permanently from straight to curled, or from curled to straight, for example, by subjecting the hair to the action of a reducing lotion which relaxes the hair by rupturing the disulfide bonds in the keratin of the hair to produce free sulfhydryl groups, followed by setting the hair in a desired configuration and then by oxidizing, or neutralizing, the hair to recreate disulfide bonds which hold the hair in the desired configuration.

Over the years, a number of reducing agents have been proposed and used in the permanent waving or straightening of hair. The agents most used today are the thioglycolates, such as ammonium thioglycolate, which are preferred because of their effectiveness in spite of the fact that they may have an irritant effect on the scalp and surrounding skin.

Sulfite and bisulfite salts, such as sodium and ammonium sulfites and bisulfites, are known to be useful as relaxing agents in hair waving or straightening and are known to be generally less irritating than the thioglycolates, but are not used as frequently as the thioglycolates because they are not sufficiently reliable to impart and hold a desired hair style in hair which is resistant to permanent waving.

Another problem in permanent waving or straightening is that the treatment frequently leaves the hair in a dry and brittle state. In addition, hair is frequently exposed to other conditions, such as sunlight, chlorinated water and harsh detergents, which tend to embrittle the hair. It is desired that a hair waving or straightening treatment not only impart a stable hair style, but also leave the hair with improved appearance, feel, condition, and ease of combing. The latter is of even greater importance for those users of hair waving or straightening treatments who also color their hair. Thus, there is a need for improved hair waving or straightening compositions which additionally condition the hair during the waving or straightening process and leave the hair soft and manageable.

In the past, hair conditioning has usually been achieved by the application of suitable conditioning products after the completion of the hair waving or conditioning process, either in a hair rinse product or in the setting of the final coiffure. These materials, when water soluble, are removed by subsequent shampooing or rinsing and their effect is thus short-lived.

Water insoluble materials have been used, particularly in the final hair set, but these require the use of organic solvents both in their application and in their removal; and organic solvents tend to extract natural constituents from the hair.

A water soluble mink oil fatty acid based quaternary ammonium salt, sold under the mark CERAPHYL 65 by Van Dyk Company, Inc., Belville, N.J., has been known to act as a hair and skin conditioner and is useful in shampoos and in post-shampoo conditioners. It has not been used or suggested as a component of a hair reducing lotion. Nor was there any reason to believe that its conditioning action would carry through from the reducing step to the final finished coiffure because most quaternary salt hair conditioners are removed when the hair is rinsed and are not carried through to the finished coiffure if applied in the reducing lotion.

SUMMARY OF THE INVENTION

It has now been discovered that the configuration of the hair can be effectively and reliably changed and its condition improved by a hair waving or straightening process in which the reducing, or relaxer, composition contains a reducing agent which is a sulfite, or bisulfite of sodium or ammonium, and as a conditioning agent, a mink oil fatty acid based quaternary ammonium salt. The compositions of this invention do not form a heavy deposit on the hair fiber nor do they leave the hair with a coated undesirable feel.

In accordance with the present invention, a hair waving or straightening composition of the present invention is provided which generally comprises an aqueous solution of a suitable reducing agent comprising from about 0.5 to about 15 percent by weight of ammonium or sodium sulfite or bisulfite, capable of acting on the keratinaceous protein of the hair to effect splitting of the disulfide bonds in the protein and the creation of sulfhydryl groups capable of bonding to each other upon oxidation to recreate disulfide groups, and a mink oil fatty acid based quaternary ammonium salt as the conditioning agent. When the composition is applied to the hair, subsequent distortion of the hair strands by winding the hair around rollers changes the spatial relationship of sulfhydryl groups so that upon oxidation, any particular sulfhydryl group is highly likely to be joined to a sulfhydryl group other than the one from which it was originally split, resulting in the formation of a different molecular structure in the hair strand and thereby permanently altering its configuration. The presence of the mink oil based quaternary salt conditioning agent leaves the hair in a soft, manageable state and eliminates the need for a subsequent step, thereby reducing time required for such treatment and eliminating the additional cost of a separate conditioning agent.

In addition to providing an improvement in the softness and manageability of the hair, the invention also provides an improvement in the curl provided by the permanent wave treatment. The presence of the mink oil based quaternary salt conditioning agent in the reducing lotion provides a better looking and tighter curl pattern in a permanent wave treatment than a similar treatment in which the conditioning agent is in the oxidizer, or neutralizer, instead of in the reducing lotion. Moreover, as compared with a permanent wave treatment in which the mink oil based quaternary salt is not used in either the reducing lotion or the neutralizer, the improvement is even more marked.

DETAILED DESCRIPTION OF PREFERRED EMBODIMENTS

The composition of this invention contains from about 0.5% to about 15% by weight and preferably 5% to 12% by weight of ammonium or sodium sulfite or bisulfite, as the reducing agent, and from about 0.1% to about 5% and preferably 0.2% to 2.0% a compound of the formula:

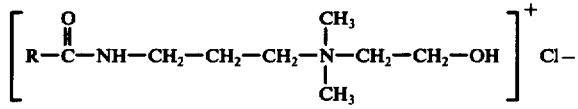

wherein R is the radical of mink oil fatty acids, as the conditioning agent. The composition can additionally include conventional additives such as coloring and perfuming agents, wetting agents, emulsifiers, opacifiers, and the like. The pH of the composition is below 7, preferably between pH 6.5 and 6.9.

The following examples further illustrate the present invention.

EXAMPLE 1

A specific waving composition was prepared by conventional procedures comprising:

|  | Percent by Weight |
| --- | --- |
| Ammonium bisulfite | 9.50 |
| Ethanol | 10.00 |
| Polyoxyethylene (20) Sorbitan Monolaurate | 0.40 |
| Perfume | 0.10 |
| Anionic surfactant | 0.10 |
| Sodium hydroxide to pH 6.9 | 6.90 |
| Water to 100 | 73.00 |

EXAMPLE 2

The above prepared lotion was divided into two equal portions. To one portion was added 0.625% by weight of a 40% solution of the mink oil fatty acid quaternary ammonium salt known as Ceraphyl 65 conditioner.

Samples of the two lotions were then used to treat several heads of hair under identical conditions. Formula with conditioner was used on one side and the formula without conditioner was used on the other side of the head to eliminate differences between patron's hair. The waving process was carried out as follows: The hair was shampooed and towel blotted. Lotion was applied to hair which was then wrapped on curlers. The wound hair was resaturated and covered with a plastic cap. The patrons were placed under a preheated hair dryer set at from about 100° to about 140° F. for about 20 minutes for normal hair and 10 minutes for tinted hair. The hair was rinsed with water and then with a 10% solution of sodium sesquicarbonate. After towel blotting and a five-minute waiting period, the hair was neutralized with a 2% solution of hydrogen peroxide followed by another five-minute waiting period. The rollers were then removed, the neutralizer worked through the hair and followed by a final water rinse.

The hair on the side treated with lotion containing the conditioner had a better curl pattern and significantly better combing and feel when both wet and dry. This improved condition was also noted on later evaluations where, after one week, the hair on the side treated with lotion containing conditioner showed better retention of the curl and a more natural look than the other side where there was no conditioner.

In a typical operation, the improved hair treatment composition of this invention can be applied to hair strands which are subsequently wrapped around rollers in the conventional manner or are subjected to the heat assist method set forth in U.S. Pat. No. 3,885,577.

Mink oil and its fatty acids are unique among animal-derived fats and oils. The total unsaturated fatty acids in mink oil account for more than 75% of the fatty acid content, but the oil, nevertheless, has a greater oxidative stability (resistance to rancidity) by the Active Oxygen Method than other animal or vegetable oils. Mink oil contains an unusually high amount of palmitoleic acid (15–19 percent), a $C_{16}$ unsaturate found in no other commonly used cosmetic ingredient.

While the invention has been described with respect to particular embodiments, it will be understood by those skilled in the art that modification and variations may be employed without departing from the scope of the invention.

We claim:

1. A hair treating composition comprising in an aqueous medium from about 0.5 to about 15% by weight of a reducing agent selected from the group consisting of ammonium sulfite, sodium sulfite, ammonium bisulfite and sodium bisulfite, and from about 0.17 to about 5.0% by weight of a mink oil fatty acid based quaternary ammonium salt, said composition having a pH of between 6.5 and 6.9, inclusive.

2. The composition of claim 1 wherein said mink oil fatty acid based quaternary ammonium salt is represented by the formula:

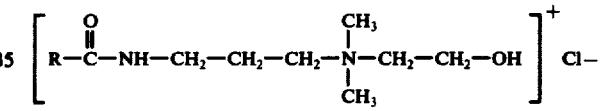

wherein R is the radical of mink oil fatty acids.

3. The composition of claim 1 wherein said reducing agent is present in an amount of from 5 to 12 percent by weight and said quaternary ammonium salt is present in an amount of from 0.2 to 2.0 percent by weight.

4. The composition of claim 1 wherein said reducing agent is ammonium bisulfite.

5. The composition of claim 1 wherein said reducing agent is sodium bisulfite.

6. The composition of claim 1 wherein said reducing agent is ammonium sulfite.

7. The composition of claim 1 wherein said reducing agent is sodium sulfite.

8. A method of imparting a new stable configuration to the hair which comprises applying to the hair the composition of claim 1, setting the hair in a desired configuration, rinsing the hair and thereafter applying an oxidizing solution to the hair while said hair is maintained in said desired configuration.

9. The method of claim 8 wherein said desired configuration is a curled configuration and said hair is maintained on curlers.

10. The method of claim 8 wherein said desired configuration is a straight configuration and said hair is combed while wetted with said composition.

* * * * *